United States Patent
Bretschneider et al.

(10) Patent No.: US 6,335,325 B1
(45) Date of Patent: Jan. 1, 2002

(54) ACYLATED 4-AMINOPYRIDINE DERIVATIVES AS PESTICIDES AND FUNGICIDES

(75) Inventors: Thomas Bretschneider, Lohmar; Markus Heil, Leverkusen; Bernd Alig, Königswinter; Gerd Kleefeld, Neuss; Christoph Erdelen, Leichlingen; Andreas Turberg, Haan; Norbert Mencke, Leverkusen, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/554,152
(22) PCT Filed: Oct. 31, 1998
(86) PCT No.: PCT/EP98/06908
§ 371 Date: May 9, 2000
§ 102(e) Date: May 9, 2000
(87) PCT Pub. No.: WO99/25691
PCT Pub. Date: May 27, 1999

(30) Foreign Application Priority Data

Nov. 14, 1997 (DE) .............................. 197 50 403

(51) Int. Cl.[7] ..................... C07D 401/12; C07D 213/75; A01N 43/40
(52) U.S. Cl. ..................... 514/211.15; 514/335; 514/340; 514/342; 514/352; 540/544; 546/261; 546/269.7; 546/269.1; 546/297
(58) Field of Search .................... 514/335, 340, 514/342, 352, 211.15; 540/544; 546/261, 269.1, 269.7, 297

(56) References Cited

U.S. PATENT DOCUMENTS 5,399,564 A    3/1995   Hackler et al. ............... 514/313
5,597,836 A    1/1997   Hackler et al. ............... 514/352
5,763,463 A  * 6/1998   Takefuji et al. .............. 514/352

FOREIGN PATENT DOCUMENTS

WO    96/08475    3/1996
WO    96/14301    5/1996

OTHER PUBLICATIONS

J.A.C.S., 78, Oct. 20, 1956, pp. 5614–5420, Sarel et al, The Synthesis Of Branched Primary and Secondary Alkyl Acetates.
J.A.C.S., 79, May 20, 1957, pp. 2530–2533, Tsai et al, Steric Effects in Hydrolysis of Hindered Amides and Nitriles.

* cited by examiner

Primary Examiner—Mukund J. Shah
Assistant Examiner—Thomas McKenzie
(74) Attorney, Agent, or Firm—Joseph C. Gil; Jackie Ann Zurcher

(57) ABSTRACT

The present application relates to novel acylated 4-aminopyridine derivatives

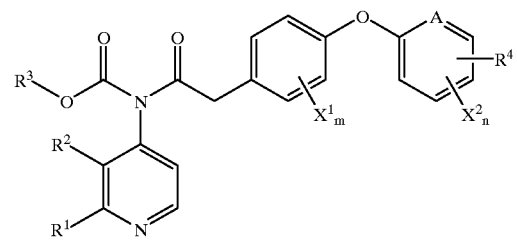

in which
$R^1$, $R^2$, $R^3$, $R^4$, A, $X^1$, $X^2$, m and n are as defined in the description,
to process for their separation and to their use for controlling animal pests and as fungicides.

18 Claims, No Drawings

ACYLATED 4-AMINOPYRIDINE DERIVATIVES AS PESTICIDES AND FUNGICIDES

The present application relates to novel acylated 4-amino-pyridine derivatives, to processes for their preparation and to their use for controlling animal pests and as fungicides.

It is already known that certain substituted 4-amino-pyridines have insecticidal properties (cf., for example, WO 93/04580, WO 96/08475, WO 96/10016, WO 96/14301 or WO 96/33975).

However, in particular at low application rates and concentrations, the activity and/or activity spectrum of these compounds is not always entirely satisfactory.

This invention provides novel acylated 4-amino-pyridines of the formula (I)

(I)

in which $R^1$ represents alkyl, halogenoalkyl, alkoxy, alkylthio, alkoxyalkyl, alkylthioalkyl or optionally substituted cycloalkyl, $R^2$ represents hydrogeni, alkyl, alkoxy, halocen, cyano, aminothiocarbonyl or optionally substituted aryl, $R^3$ represents alkyl, alkenyl, optionally substituted cycloalkyl or represents in each case optionally substituted aryl or arylalkyl, $R^4$ represents one of the radicals —CO—$NR^5R^6$, —CS—$NR^7R^8$, —C(=NH)—NH—$OR^9$, —C(=N—OH)—OH, —CHO, —CH=N—$OR^{10}$ and —C(=N—$OR^{11}$)—$R^{12}$ or represents an optionally substituted heterocycle where $R^5$ to $R^{12}$ independently of one another represent hydrogen or alkyl, A represents CH, $CX^2$ or N, $X^1$ and $X^2$ independently of one another represent halogen, alkyl, alkoxy or halogenoalkyl and m represents 0, 1, 2, 3 or 4, n represents 0, 1, 2 or 3 and in the case A=$CX^2$ also represents 4, including the pyridine N-oxides and salts which are protonated at the pyridine nitrogen.

Furthermore, it has been found that the compounds of the formula (I) are obtained when compounds of the formula (II)

(II)

in which $R^1$, $R^2$, $R^3$, A, $X^1$, $X^2$, m and n are as defined above are derivatized at the nitrile group by generally known methods of organic chemistry.

Finally, it has been found that the novel compounds of the formula (I) have strongly pronounced biological properties and are suitable especially as fungicides and for controlling animal pests, in particular insects, arachnids and nematodes, which are encountered in agriculture, in forests, in the protection of stored products and materials and in the hygiene sector.

Surprisingly, the acylated 4-amino-pyridines according to the invention exhibit considerably better activity against animal pests than known compounds of a similar constitution.

The formula (I) provides a general definition of the compounds according to the invention.

Preferred substituents or ranges of the radicals listed in the formulae mentioned above and below are illustrated below.

$R^1$ preferably represents $C_1$–$C_4$-alkyl, $C_1$–$C_4$-alkoxy, $C_1$–$C_4$-alkylthio, $C_1$–$C_4$-halogenoalkyl having 1 to 5 identical or different halogen atoms, $C_1$–$C_4$-alkoxy-$C_1$–$C_4$-alkyl, $C_1$–$C_4$-alkylthio-$C_1$–$C_4$-alkyl or represents $C_5$–$C_6$-cycloalkyl which is optionally mono- to trisubstituted by identical or different substituents from the group consisting of $C_1$–$C_4$-alkyl and halogen.

$R^2$ preferably represents hydrogen, $C_1$–$C_2$-alkyl, $C_1$–$C_2$-alkoxy, chlorine bromine, cyano aminothiocarbonyl or represents phenyl which is optionally mono- to trisubstituted by identical or different substituents, possible substituents being halogen, ($C_1$–$C_4$-alkyl, $C_1$–$C_4$-alkoxy and $C_1$–$C_4$-halogenoalkyl having 1 to 5 identical or different halogen atoms.

$R^3$ preferably represents $C_1$–$C_4$-alkyl, $C_2$–$C_4$-alkenyl, represents $C_5$–$C_6$-cycloalkyl which is optionally mono- to trisubstituted by identical or different substituents from the group consisting of $C_1$–$C_4$-alkyl and halogen or represents phenyl or benzyl, each of which is optionally mono- to trisubstituted by identical or different substituents, possible substituents being halogen, $C_1$–$C_4$-alkyl, $C_1$–$C_4$-alkoxy and $C_1$–$C_4$-halogenoalkyl having 1 to 5 identical or different halogen atoms.

$R^4$ preferably represents one of the radicals —CO—$NR^5R^6$, —CS—$NR^7R^8$, —C(=NH)—NH—$OR^9$, —C(=N—OH)—OH, —CHO, —CH=N—$OR^{10}$ and —C(=N—$OR^{11}$)—$R^{12}$, where $R^5$ to $R^{12}$ independently of one another represent hydrogen or $C_1$–$C_4$-alkyl;

$R^4$ also preferably represents a 5- or 6-membered saturated or unsaturated heterocycle which is optionally mono- or disubstituted by identical or different substituents from the group consisting of halogen, $C_1$–$C_4$-alkyl, $C_1$–$C_4$-alkoxy and $C_1$–$C_4$-halogenoalkyl having 1 to 5 identical or different halogen atoms and contains oxygen and/or sulphur and/or nitrogen as heteroatoms, for example 1,2,4-oxadiazol-3-yl, 1,3-thiazol-2-yl or 1,4,2-dioxazin-3-yl.

A preferably represents CH or N.

A also preferably represents $CX^2$.

$X^1$ and $X^2$ independently of one another preferably represent fluorine, chlorine, bromine, $C_1$–$C_2$-alkyl, $C_1$–$C_2$-alkoxy or $C_1$–$C_2$-halogenoalkyl having 1 to 5 identical or different halogen atoms.

m and n independently of one another preferably represent 0, 1 or 2.

Halogen (atoms) represents, for example, fluorine (atoms), chlorine (atoms) or bromine (atoms).

$R^1$ particularly preferably represents methyl, ethyl, methoxy, methylthio, 1-chloro-eth-1-yl, methoxymethyl or methylthiomethyl.

$R^2$ particularly preferably represents hydrogen, methyl, methoxy, chlorine, bromine, cyano, aminothiocarbonyl or phenyl.

$R^3$ particularly preferably represents methyl, ethyl, i-propyl, allyl, cyclohexyl, phenyl or benzyl.

$R^4$ particularly preferably represents one of the radicals
—CO—$NH_2$, —CO—$NHCH_3$, —CO—$N(CH_3)_2$,
—CS—$NH_2$, —CS—$NHCH_3$, —CS—$N(CH_3)_2$,
—C(=NH)—NH—OH, —C(=N—OH)—OH,
—CHO, —CH=N—OH, —CH=N—$OCH_3$,
—C(=N—OH)—$CH_3$ or —C(=N—$OCH_3$)—$CH_3$;

$R^4$ also particularly preferably represents 1,2,4-oxadiazol-3-yl, 1,3-thiazol-2-yl or 1,4,2-dioxazin-3-yl, each of which is optionally mono- or disubstituted by identical or different substituents from the group consisting of fluorine, chlorine, bromine, methyl, methoxy and trifluoromethyl.

A particularly preferably represents CH or N.

$X^1$ and $X^2$ independently of one another particularly preferably represent fluorine, chlorine, bromine, methyl, methoxy or trifluoromiethyl.

m particularly preferably represents 0.

n particularly preferably represents 0 or 1.

Preferred compounds according to the invention are substances of the formulae (IA), (IB), (IC) and (ID):

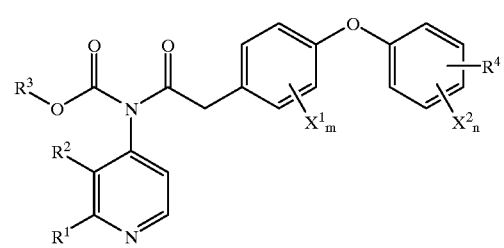

(IA)

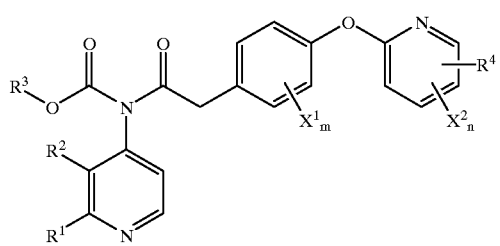

(IB)

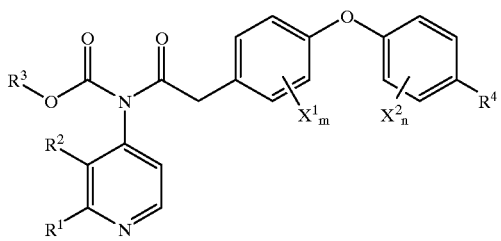

(IC)

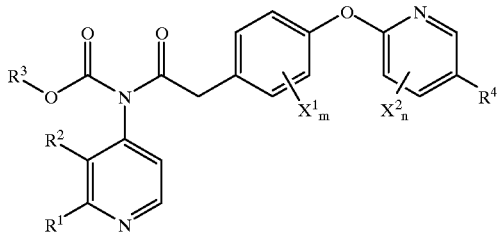

(ID)

in which $R^1$ to $R^4$, $X^1$, $X^2$, m and n have the abovementioned general, preferred and particularly preferred meanings.

Preferred compounds according to the invention are also substances of the formulae (IA-1), (IB-1), (IC-1) and (ID-1):

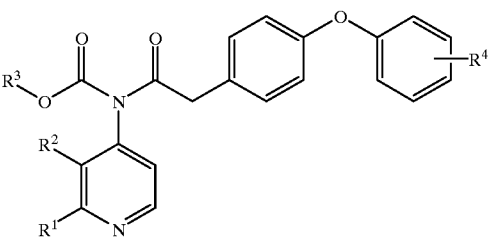

(IA-1)

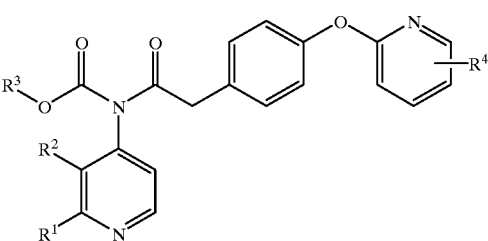

(IB-1)

-continued

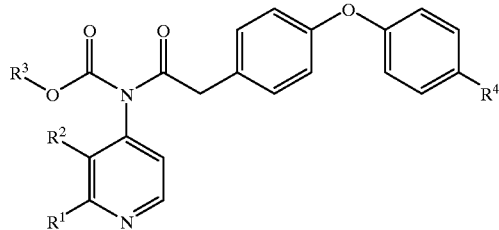
(IC-1)

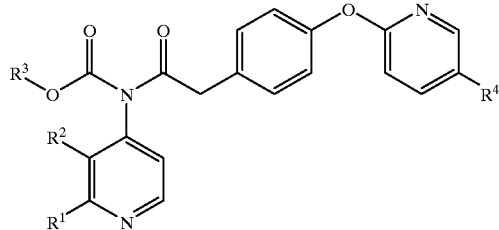
(ID-1)

in which

R¹ to R⁴ have the abovementioned general preferred and particularly preferred meanings.

The abovementioned general or preferred radical definitions or illustrations apply to the end products and, correspondingly, to the starting materials and intermediates. These radical definitions can be combined with one another at will, i.e. including combinations between the respective preferred ranges.

Preference, according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

In the radical definitions given above and below, hydrocarbon radicals, such as alkyl or alkenyl are in each case straight-chain or branched as far as this is possible—including in combination with heteroatoms such as alkoxy or alkylthio.

The following compounds of the formula (IC-1) may be mentioned in particular:

TABLE a

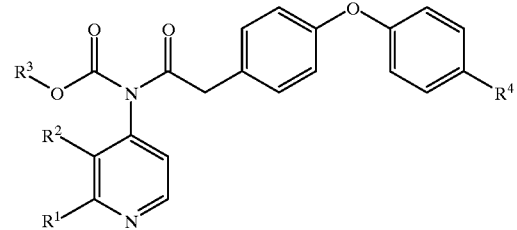
(IC-1)

| R¹ | R² | R³ | R⁴ |
|---|---|---|---|
| $C_2H_5$ | Cl | i—$C_3H_7$ | —CO—$NH_2$ |
| $C_2H_5$ | Cl | i—$C_3H_7$ | —CO—$NHCH_3$ |
| $C_2H_5$ | Cl | i—$C_3H_7$ | —CO—$N(CH_3)_2$ |
| $C_2H_5$ | Cl | i—$C_3H_7$ | —CS—$NH_2$ |

TABLE a-continued (IC-1)

| R¹ | R² | R³ | R⁴ |
|---|---|---|---|
| $C_2H_5$ | Cl | i—$C_3H_7$ | —CS—$NHCH_3$ |
| $C_2H_5$ | Cl | i—$C_3H_7$ | —CS—$N(CH_3)_2$ |
| $C_2H_5$ | Cl | i—$C_3H_7$ | —C(=NH)—NH—OH |
| $C_2H_5$ | Cl | i—$C_3H_7$ | —C(=N—OH)—OH |
| $C_2H_5$ | Cl | i—$C_3H_7$ | —CHO |
| $C_2H_5$ | Cl | i—$C_3H_7$ | —CH=N—OH |
| $C_2H_5$ | Cl | i—$C_3H_7$ | —CH=N—$OCH_3$ |
| $C_2H_5$ | Cl | i—$C_3H_7$ | —C(=N—OH)—$CH_3$ |
| $C_2H_5$ | Cl | i—$C_3H_7$ | —C(=N—$OCH_3$)—$CH_3$ |
| $C_2H_5$ | Cl | i—$C_3H_7$ | 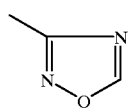 |
| $C_2H_5$ | Cl | i—$C_3H_7$ | 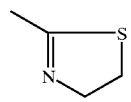 |
| $C_2H_5$ | Cl | i—$C_3H_7$ | 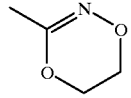 |
| $C_2H_5$ | —CN | i—$C_3H_7$ | —CO—$NH_2$ |
| $C_2H_5$ | —CN | i—$C_3H_7$ | —CO—$NHCH_3$ |
| $C_2H_5$ | —CN | i—$C_3H_7$ | —CO—$N(CH_3)_2$ |
| $C_2H_5$ | —CN | i—$C_3H_7$ | —CS—$NH_2$ |
| $C_2H_5$ | —CN | i—$C_3H_7$ | —CS—$NHCH_3$ |
| $C_2H_5$ | —CN | i—$C_3H_7$ | —CS—$N(CH_3)_2$ |
| $C_2H_5$ | —CN | i—$C_3H_7$ | —C(=NH)—NH—OH |
| $C_2H_5$ | —CN | i—$C_3H_7$ | —C(=N—OH)—OH |
| $C_2H_5$ | —CN | i—$C_3H_7$ | —CHO |
| $C_2H_5$ | —CN | i—$C_3H_7$ | —CH=N—OH |
| $C_2H_5$ | —CN | i—$C_3H_7$ | —CH=N—$OCH_3$ |
| $C_2H_5$ | —CN | i—$C_3H_7$ | —C(=N—OH)—$CH_3$ |
| $C_2H_5$ | —CN | i—$C_3H_7$ | —C(=N—$OCH_3$)—$CH_3$ |
| $C_2H_5$ | —CN | i—$C_3H_7$ | 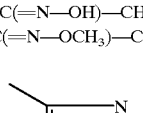 |
| $C_2H_5$ | —CN | i—$C_3H_7$ | 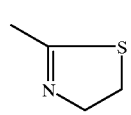 |
| $C_2H_5$ | —CN | i—$C_3H_7$ | 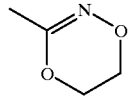 |

TABLE a-continued

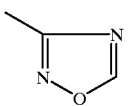
(IC-1)

| R¹ | R² | R³ | R⁴ |
|---|---|---|---|
| $C_2H_5$ | —CS—$NH_2$ | i—$C_3H_7$ | —CO—$NH_2$ |
| $C_2H_5$ | —CS—$NH_2$ | i—$C_3H_7$ | —CO—$NHCH_3$ |
| $C_2H_5$ | —CS—$NH_2$ | i—$C_3H_7$ | —CO—$N(CH_3)_2$ |
| $C_2H_5$ | —CS—$NH_2$ | i—$C_3H_7$ | —CS—$NH_2$ |
| $C_2H_5$ | —CS—$NH_2$ | i—$C_3H_7$ | —CS—$NHCH_3$ |
| $C_2H_5$ | —CS—$NH_2$ | i—$C_3H_7$ | —CS—$N(CH_3)_2$ |
| $C_2H_5$ | —CS—$NH_2$ | i—$C_3H_7$ | —C(=NH)—NH—OH |
| $C_2H_5$ | —CS—$NH_2$ | i—$C_3H_7$ | —C(=N—OH)—OH |
| $C_2H_5$ | —CS—$NH_2$ | i—$C_3H_7$ | —CHO |
| $C_2H_5$ | —CS—$NH_2$ | i—$C_3H_7$ | —CH=N—OH |
| $C_2H_5$ | —CS—$NH_2$ | i—$C_3H_7$ | —CH=N—$OCH_3$ |
| $C_2H_5$ | —CS—$NH_2$ | i—$C_3H_7$ | —C(=N—OH)—$CH_3$ |
| $C_2H_5$ | —CS—$NH_2$ | i—$C_3H_7$ | —C(=N—$OCH_3$)—$CH_3$ |
| $C_2H_5$ | —CS—$NH_2$ | i—$C_3H_7$ | 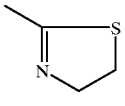 |
| $C_2H_5$ | —CS—$NH_2$ | i—$C_3H_7$ | 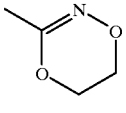 |
| $C_2H_5$ | —CS—$NH_2$ | i—$C_3H_7$ | 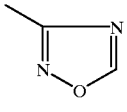 |
| —$CH_2OCH_3$ | —$OCH_3$ | i—$C_3H_7$ | —CO—$NH_2$ |
| —$CH_2OCH_3$ | —$OCH_3$ | i—$C_3H_7$ | —CO—$NHCH_3$ |
| —$CH_2OCH_3$ | —$OCH_3$ | i—$C_3H_7$ | —CO—$N(CH_3)_2$ |
| —$CH_2OCH_3$ | —$OCH_3$ | i—$C_3H_7$ | —CS—$NH_2$ |
| —$CH_2OCH_3$ | —$OCH_3$ | i—$C_3H_7$ | —CS—$NHCH_3$ |
| —$CH_2OCH_3$ | —$OCH_3$ | i—$C_3H_7$ | —CS—$N(CH_3)_2$ |
| —$CH_2OCH_3$ | —$OCH_3$ | i—$C_3H_7$ | —C(=NH)—NH—OH |
| —$CH_2OCH_3$ | —$OCH_3$ | i—$C_3H_7$ | —C(=N—OH)—OH |
| —$CH_2OCH_3$ | —$OCH_3$ | i—$C_3H_7$ | —CHO |
| —$CH_2OCH_3$ | —$OCH_3$ | i—$C_3H_7$ | —CH=N—OH |
| —$CH_2OCH_3$ | —$OCH_3$ | i—$C_3H_7$ | —CH=N—$OCH_3$ |
| —$CH_2OCH_3$ | —$OCH_3$ | i—$C_3H_7$ | —C(=N—OH)—$CH_3$ |
| —$CH_2OCH_3$ | —$OCH_3$ | i—$C_3H_7$ | —C(=N—$OCH_3$)—$CH_3$ |
| —$CH_2OCH_3$ | —$OCH_3$ | i—$C_3H_7$ | 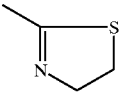 |
| —$CH_2OCH_3$ | —$OCH_3$ | i—$C_3H_7$ | 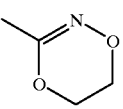 |
| —$CH_2OCH_3$ | —$OCH_3$ | i—$C_3H_7$ | 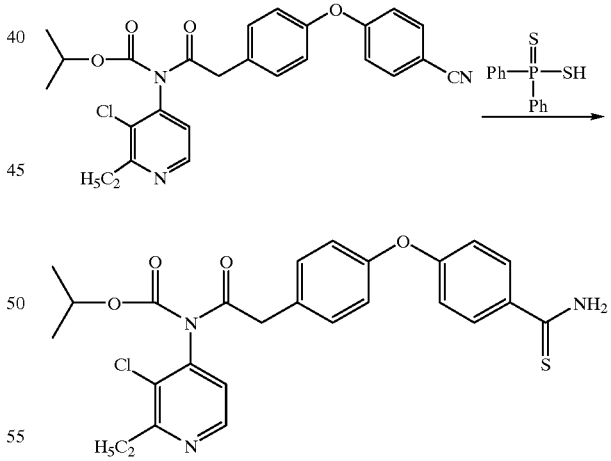 |

Using, for example, N-(3-chloro-2-ethyl-pyridin-4-yl)-N-isopropoxycarbonyl-4-(4-cyanophenoxy)phenylacetamide as starting material and diphenyldithiophosphinic acid as derivatizing (sulphurizing) agent, the course of the process according to the invention can be represented by the following reaction scheme:

The compounds of the formula (II) required as starting materials for carrying out the process according to the invention are known (cf. WO 96/33975) and/or can be obtained by the processes described therein.

The compounds of the formula (I) according to the invention can also be obtained in a generally known manner (cf. WO 96/33975 and WO 93/04580) according to the following general reaction scheme 1:

Reaction scheme 1

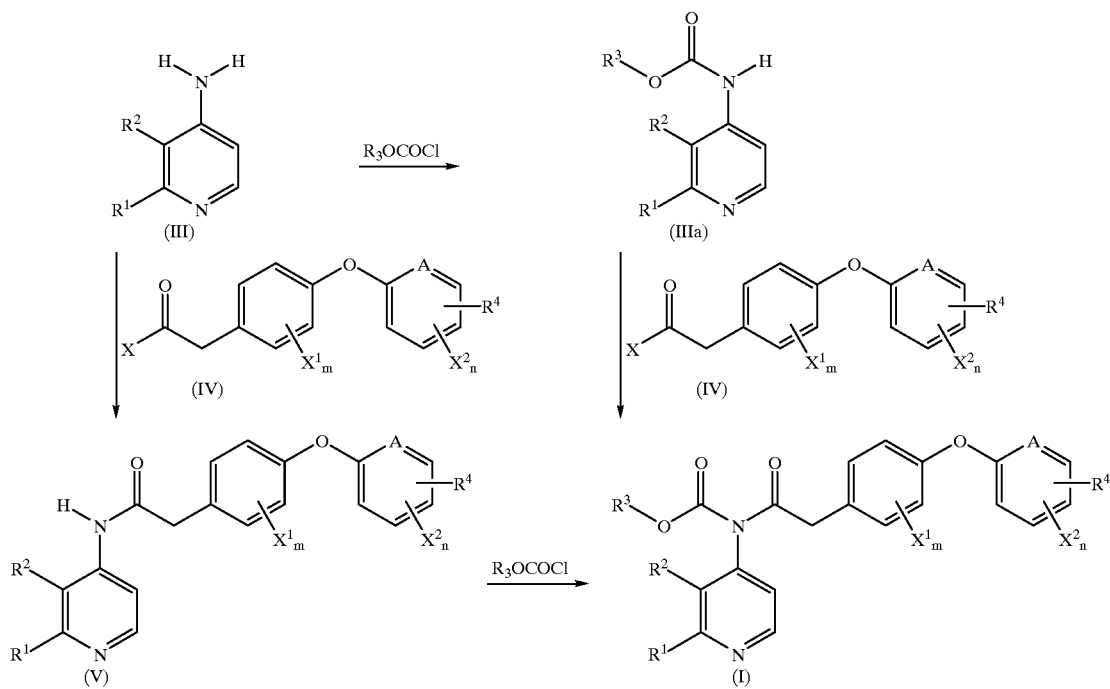

where $R^1$ to $R^4$, A, $X^1$, $X^2$, m and n are as defined above and

X represents a leaving group, for example halogen, in particular chlorine or bromine.

The derivatization of the nitrile group according to the process according to the invention, i.e. the synthesis of compounds in which $R^4$ represents the radicals according to the invention, can in principle also be carried out as early as at the stages according to compounds of the formulae (IV) and (V) mentioned in reaction scheme 1.

The synthesis steps required to this end are standard methods of organic chemistry and generally known from the literature—cf. also the general reaction scheme 2 below:

Reaction scheme 2

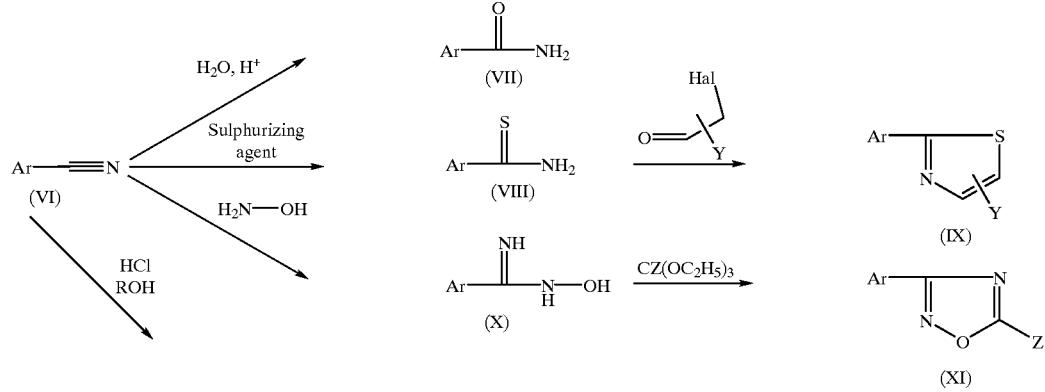

-continued $$Ar-\overset{O}{\underset{(XII)}{C}}-OR \xrightarrow[NaOCH_3]{H_2N-OH} Ar-\overset{N-OH}{\underset{(XIII)}{C}}-OH \xrightarrow{Br-CH_2-CH_2-Br} Ar-\underset{(XIV)}{\text{[1,4,2-dioxazine ring]}}$$

where Ar represents the following radicals:

a) (According to Formula II)

b) (According to Formula IV)

c) (According to Formula V)

and

Hal represents halogen, preferably chlorine or bromine,

R represents $C_1-C_4$-alkyl, preferably methyl, ethyl, n- or i-propyl and

Y and Z represent, for example, halogen, $C_1-C_4$-alkyl, $C_1-C_4$-alkoxy or $C_1-C_4$-halogenoalkyl having 1 to 5 identical or different halogen atoms, particularly preferably represent fluorine, chlorine, bromine, methyl, methoxy or trifluoromethyl.

Aromatic nitriles (VI) can be converted, for example, by hydrolysis into the carboxamides (VII) (cf., for example, JACS 78, 5416 (1956) and 79, 2530 (1957)).

Using sulphurizing agents such as, for example, phosphorus pentasulphide, Lawessons reagent or diphenylditliophosphinic acid [$Ph_2P(=S)$—SH, cf., for example, THL 1851 (1981)], it is possible to convert aromatic nitrites (VI) into the thioamides (VIII) (cf., for example, Sulphur reports 297 (1992)).

The Hantzsch synthesis of the thiazoles (IX) by reaction of the thioamides (VIII) with halogenoketones is a standard reaction of organic chemistry.

The 1,2,4-oxadiazoles (XI) are obtained by reacting the aromatic nitriles (VI) with hydroxylamine to (Tite the compounds (X), followed by cyclization with appropriate ortho esters.

Reaction of the carboxylic esters (XII), obtainable from the aromatic nitrites (VI) by Pinner reaction, with hydroxylamine and sodium ethoxide to give the compounds (XIII) and subsequent cyclization with dibromoethane gives 1,4,2-dioxazines (XIV).

The pyridine N-oxides and the salts of the compounds of the formula (I) which are protonated at the pyridine nitrogen can be obtained in a generally customary and known manner, for example by reacting the compounds of the formula (I) with an oxidizing agent such as, for example, m-chloroperbenzoic acid or with organic or inorganic acids such as, for example, trifluoroacetic acid, hydrogen bromide or hydrogen chloride.

Work-up and isolation of the intermediates and end products in question is carried out in a generally known manner.

The active compounds, having good crop tolerance and homeotherm safety, are suitable for controlling animal pests, in particular insects, arachnids and nematodes, which are encountered in agriculture, in forests, in the protection of stored products and of materials, and in the hygiene sector. They are preferably used as crop protection agents. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella germanica, Acheta domesticus,* Gryllotalpa spp., *Locusta migratoria migratorioldes, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the liomoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix*, Pemphligus spp., *Macrosiphum avenae*, Myzus spp., *Phorodon humuli, Rhopalosiphumn padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Spodoptera litura*, Spodoptera spp., *Trichoplusia ni, Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium puinctatum, Rhizopertha dominica, Bruchidius obtectus, Acanthoscelides obtectus, Hylotrupes bajulus*, Agelastica alni, *Leptinotarsa decemlineata, Phaedon cochleariae*, Diabrotica spp., *Psylliodes chrysocephala, Epilachna varivestis*, Atomaria spp., *Oryzaephilus sunnamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica*.

From the order of the Hymenoptera, for example, Diprion spp., Hoplocampa spp., Lasius spp., *Monomonrium pharaonis* and Vespa spp.

From the order of the Diptera, for example, Aedes spp., Anopheles spp., Culex spp., *Drosophilla melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., (O)estrus spp., Hypodemia spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp.

The compounds of the formula (I) according to the invention are notable in particular for a good insecticidal and acaricidal action.

They can be employed particularly successfully for controlling phytopathogenic insects, such as, for example, against the caterpillars of the owlet moth (*Spodoptera exigua*).

The active compounds can be converted into the customary formulations such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

If the extender used is water, it is also possible to employ for example organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates as well as protein hydrolysates; as dispersing agents there are suitable: for example lignini-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound of the invention can be present in its commercially customary formulations and in the use forms prepared from these formulations, in a mixture with other active compounds, such as insecticides, attractants, sterilants, bactericides, acaricides, nematicides, fungicides, growth regulators or herbicides. The insecticides include, for example, phosphates, carbamates, carboxylates, chlorinated hydrocarbons, phenylureas, substances produced by microorganisms, etc.

Particularly favourable co-components are, for example, those listed below:

Fungicides:
  2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazole, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole. methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides:
  bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaricides/Nematicides:
  abamnectin, AC 303 630, acephate, acrinathrin, alanycarb, aldicarb, alphamethrin, amitraz, avermectin, AZ 60541, azadirachtin, azinphos A, azinphos M, azocyclotin. *Bacillus thuringiensis*, bendiocarb, benfuracarb, bensultap, beta-cyfluthrin, bifenthrin, BPMC, brofenprox, bromophos A, bufencarb, buprofezin, butocarboxim, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethotenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos,

RH 5992, salithion, sebufos, silafluofen, sulphotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators, is also possible.

The active compounds according to the invention can furthermore be present in their commercially available formulations and in the use forms prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the suborders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order of the Diptera and the suborders of the Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaca spp., Stomoxys spp., Haemcitobia spp., Morellia spp., Fannia spp., Glossina spp., Calliphora spp., Lucilia spp., Chrysonmyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the subclass of the Acaria (Acarida) and the orders of the Meta- and Mesostigmrata, for example Argas spp., Ornithodorus spp., Otobius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according( to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Denidrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec., *Dinoderus minutus.*

Dermapterans, such as

*Sirex juvencus, Urocerus gigas, Urocerpus gioas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristiletals, such as Lepisma saccarina.

Industrial materials are to be understood as meaning, in the present context, non-living materials such as, preferably , synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters, such as tributyl phosphate, adipic esters, such as di-(2-ethylhexyl) adipate, stearates, such as butyl stearate or amyl stearate, oleates, such as butyl oleate, glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise further insecticides and additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinylbutyl carbamate, N-octyl-isothiazolin-3-one and 4,5-dichloro-N-octylisothiazolin-3-one.

The active compounds according to the invention also have potent microbicidal activity and can be employed practically for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea (conidia form: Drechslera, syn: Helminthosporium);*

Cochliobolus species, such as, for example, *Cochliobolus sativus (conidia form: Drechslera, syn: Helminthosporium);*

Uromyces species, such as, for example, *Uromyces appendiculatus;*

Puccinia species, such as, for example, *Puccinia recondita;*

Sclerotinia species, such as, for example, *Sclerotinia sclerotiorum*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;* and

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

In addition, they have broad in vitro activity against phytopathogenic fungi.

When used as fungicides, the active compounds according to the invention can be employed as such, in the form of their commercial formulations or as the use forms prepared therefrom, such as ready-to-use solutions, suspensions, wettable powders, pastes, soluble powders, dusts and granules. They are applied in the customary manner, for example by watering, spraying, atomizing, scattering, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range: in general, they are between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0. 1% by weight, preferably from 0.0001 to 0.02% by weight, are required at the treatment site.

The preparation and the use of the active compounds according to the invention is illustrated by the following examples.

PREPARATION EXAMPLES

Example 1

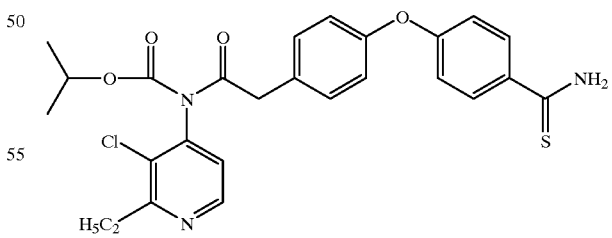

0.96 g (2 mmol) of N-(3-chloro-2-ethyl-pyridin-4-yl)-N-isopropoxycarbonyl-4-(4-cyanophenoxy)phenylacetamide (cf. WO 96/33975) and 1 g (4 mmol) of diphenyldithiophosphinic acid are stirred in 10 ml of isopropanol at 60° C. for 3 hours and subsequently concentrated.

Chromatographic purification over silica gel (chloroform/acetone 95/5) gives 0.28 g (27% of theory) of N-(3-chloro- 2-ethyl-pyridin-4-yl)-N-isopropoxycarbonyl-4-(4-aminothiocarbonylphenoxy)-phenylacetamide of logP (pH2)=3.71.

$^1$H-NMR (CDCl$_3$): 1.15 (d, 6H), 1.3 (t, 3H), 3.0 (q, 2H), 4.4 (s, 2H), 5.0 (m, 1H), 6.95 (m, 5H), 7.1 (brd, 1H), 7.25 (m, 2H), 7.5 (brd, 1H), 7.9 (m, 2H) and 8.5 (d, 1H) ppm.

[logP=The logP values were determined in accordance with EEC Directive 79/831 Annex V. A8 by HPLC (gradient method, acetonitrile/0.1% strength aqueous phosphoric acid]

USE EXAMPLES

In the Use Examples below, the compound of the formula (A)

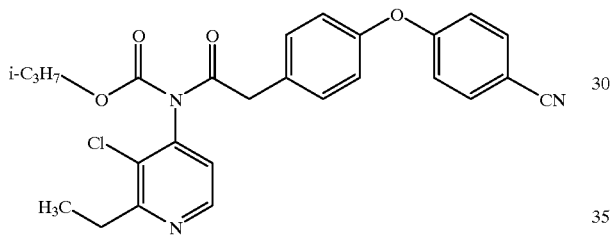

known from WO 96/33975 was used as comparative substance.

Example A

*Spodoptera exigua* Test

Solvent: 7 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and populated with caterpillars of the owlet moth (*Spodoptera exigua*) whilst the leaves are still moist.

After the desired period of time, the kill in % is determined. 100% means that all caterpillars have been killed; 0% means that none of the caterpillars have been killed.

In this test, at an exemplary active compound concentration of 0.0008%, the compound of Preparation Example 1 effected a kill of 100%, whereas the known compound (A) effected a kill of only 50%, in each case after 6 days.

What is claimed is:
1. A compound of formula (I)

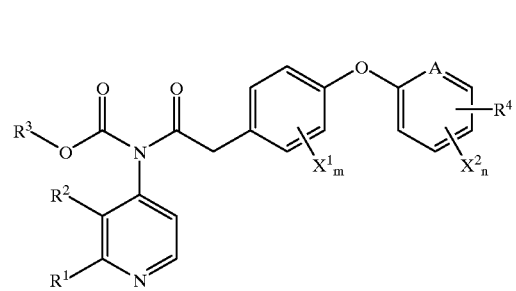

in which
R$^1$ represents C$_1$–C$_4$-alkyl, C$_1$–C$_4$-alkoxy, C$_1$–$_4$-alkylthio, C$_1$–C$_4$-halogenoalkyl having 1 to 5 identical or different halogen atoms, C$_1$–C$_4$-alkoxy-C$_1$–C$_4$-alkyl, C$_1$–C$_4$-alkylthio-C$_1$–C$_4$-alkyl or represents C$_5$–C$_6$-cycloalkyl which is optionally mono- to trisubstituted by identical or different substituents from the group consisting of C$_1$–C$_4$-alkyl and halogen, R$^2$ represents hydrogen, C$_1$–C$_2$-alkyl, C$_1$–C$_2$-alkoxy, chlorine, bromine, cyano, aminothiocarbonyl or represents phenyl which is optionally mono- to trisubstituted by identical or different substituents, possible substituents being halogen, C$_1$–C$_4$-alkyl, C$_1$–C$_4$-alkoxy and C$_1$–C$_4$-halogenoalkyl having 1 to 5 identical or different halogen atoms, R$^3$ represents C$_1$–C$_4$-alkyl, C$_2$–C$_4$-alkenyl, represents C$_5$–C$_6$-cycloalkyl which is optionally mono- to trisubstituted by identical or different substituents from the group consisting of C$_1$–C$_4$-alkyl and halogen or represents phenyl or benzyl, each of which is optionally mono- to trisubstituted by identical or different substituents, possible substituents being halogen, C$_1$–C$_4$-alkyl, C$_1$–C$_4$-alkoxy and C$_1$–C$_4$-halogenoalkyl having 1 to 5 identical or different halogen atoms, R$^4$ represents one of the radicals —CO—NR$^5$R$^6$, —CS—NR$^7$R$^8$, —C(=NH)—NH—OR$^9$, —C(=N—OH)—OH, —CHO, —CH=N—OR$^{10}$ and —C(=N—OR$^{11}$)—R$^{12}$, where
R$^5$ to R$^{12}$ independently of one another represent hydrogen or C$_1$–C$_4$-alkyl, or R$^4$ represents a 5- or 6-membered saturated or unsaturated heterocycle which is optionally mono- or disubstituted by identical or different substituents from the group consisting of halogen, C$_1$–C$_4$-alkyl, C$_1$–C$_4$-alkoxy and C$_1$–C$_4$-halogenoalkyl having 1 to 5 identical or different halogen atoms and contains oxygen and/or sulphur and/or nitrogen as heteroatoms, A represents CH or N, or
A represents CX$^2$, where
X$^1$ and X$^2$ independently of one another represent fluorine, chlorine, bromine, C$_1$–C$_2$-alkyl, C$_1$–C$_2$-alkoxy or C$_1$–C$_2$-halogenoalkyl having 1 to 5 identical or different halogen atoms, m represents 0, 1, 2, 3 or 4,
n represents 0, 1, 2 or 3 and in the case A=CX$^2$ also represents 4, including the pyridine N-oxides and salts which are protonated at the pyridine nitrogen.

2. The compound of the formula (I)

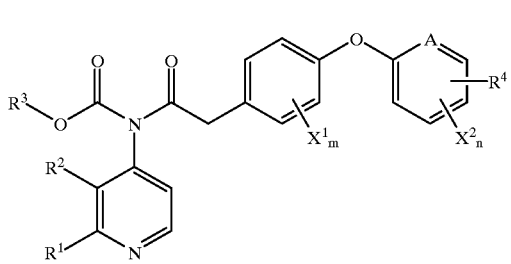

(I)

in which
- $R^1$ represents $C_1$–$C_4$-alkyl, $C_1$–$C_4$-alkoxy, $C_1$–$C_4$-alkylthio, $C_1$–$C_4$-halogenoalkyl having 1 to 5 identical or different halogen atoms, $C_1$–$C_4$-alkoxy-$C_1$–$C_4$-alkyl, $C_1$–$C_4$-alkylthio-$C_1$–$C_4$-alkyl or represents $C_5$–$C_6$-cycloalkyl which is optionally mono- to trisubstituted by identical or different substituents from the group consisting of $C_1$–$C_4$-alkyl and halogen,
- $R^2$ represents hydrogen, $C_1$–$C_2$-alkyl, $C_1$–$C_2$-alkoxy, chlorine, bromine, cyano, aminothiocarbonyl or represents phenyl which is optionally mono- to trisubstituted by identical or different substituents, possible substituents being halogen, $C_1$–$C_4$-alkyl, $C_1$–$C_4$-alkoxy and $C_1$–$C_4$-halogenoalkyl having 1 to 5 identical or different halogen atoms,
- $R^3$ represents $C_1$–$C_4$-alkyl, $C_2$–$C_4$-alkenyl, represents $C_5$–$C_6$-cycloalkyl which is optionally mono- to trisubstituted by identical or different substituents from the group consisting of $C_1$–$C_4$-alkyl and halogen or represents phenyl or benzyl, each of which is optionally mono- to trisubstituted by identical or different substituents, possible substituents being halogen, $C_1$–$C_4$-alkyl, $C_1$–$C_4$-alkoxy and $C_1$–$C_4$-halogenoalkyl having 1 to 5 identical or different halogen atoms,
- $R^4$ represents one of the radicals —CO—$NR^5R^6$, —CS—$NR^7R^8$, —C(=NH)—NH—$OR^9$, —C(=N—OH)—OH, —CHO, —CH=N—$OR^{10}$ and —C(=N—$OR^{11}$)—$R^{12}$,
  where
  $R^5$ to $R^{12}$ independently of one another represent hydrogen or $C_1$–$C_4$-alkyl, or
- $R^4$ represents a 5- or 6-membered saturated or unsaturated heterocycle which is optionally mono- or disubstituted by identical or different substituents from the group consisting of halogen, $C_1$–$C_4$-alkyl, $C_1$–$C_4$-alkoxy and $C_1$–$C_4$-halogenoalkyl having 1 to 5 identical or different halogen atoms and contains oxygen and/or sulphur and/or nitrogen as heteroatoms
- A represents CH or N, or
- A represents $CX^2$, where
  $X^1$ and $X^2$ independently of one another represent fluorine, chlorine, bromine, $C_1$–$C_2$-alkyl, $C_1$–$C_2$-alkoxy or $C_1$–$C_2$-halogenoalkyl having 1 to 5 identical or different halogen atoms,
- m and n independently of one another represent 0, 1 or 2, including the pyridine N-oxides and salts which are protonated at the pyridine nitrogen.

3. The compound of the formula (I) according to claim 2 in which
- $R^1$ represents methyl, ethyl, methoxy, methylthio, 1-chloro-eth-1-yl, methoxymethyl or methylthiomethyl,
- $R^2$ represents hydrogen, methyl, methoxy, chlorine, bromine, cyano, aminothiocarbonyl or phenyl,
- $R^3$ represents methyl, ethyl, i-propyl, allyl, cyclohexyl, phenyl or benzyl,
- $R^4$ represents one of the radicals —CO—$NH_2$, —CO—$NHCH_3$, —CO—$N(CH_3)_2$, —CS—$NH_2$, —CS—$NHCH_3$, —CS—$N(CH_3)_2$, —C(=NH)—NH—OH, —C(=N—OH)—OH, —CHO, —CH=N—OH, —CH=N—$OCH_3$, —C(=N—OH)—$CH_3$ or —C(=N—$OCH_3$)—$CH_3$, or
- $R^4$ represents 1,2,4-oxadiazol-3-yl, 1,3-thiazol-2-yl or 1,4,2-dioxazin-3-yl, each of which is optionally mono- or disubstituted by identical or different substituents from the group consisting of fluorine, chlorine, bromine, methyl, methoxy and trifluoromethyl,
- A represents CH or N, or
- A represents $CX^2$, where
  $X^1$ and $X^2$ represent fluorine, chlorine, bromine, methyl, methoxy or trifluoromethyl,
- m represents 0, and
- n represents 0 or 1, including the pyridine N-oxides and salts which are protonated at the pyridine nitrogen.

4. A compound according to claim 2 wherein $R^4$ represents 1,2,4-oxadiazol-3-yl, 1,3-thiazol-2-yl or 1,4,2-dioxazin-3-yl.

5. A pesticide and fungicide formulation comprising at least one compound of the formula (I) according to claim 1 and an extender and/or a surfactant.

6. A pesticide and fungicide formulation, comprising at least one compound of the formula (I) according to claim 2 and an extender and/or a surfactant.

7. A method for controlling pests and fungi comprising applying a compound of the formula (I) according to claim 1 to pests or fungi and/or their habitat, wherein the pests are selected from the group consisting of insects, arachnids, nematodes and mixtures thereof.

8. A method for controlling pests and fungi comprising applying a compound of the formula (I) according to claim 2 to pests or fungi and/or their habitat, wherein the pests are selected from the group consisting of insects, arachnids, nematodes and mixtures thereof.

9. A process for preparing a compound of the formula (I) according to claim 1, comprising the step of replacing the nitrile group of thecompound of the formula (II)

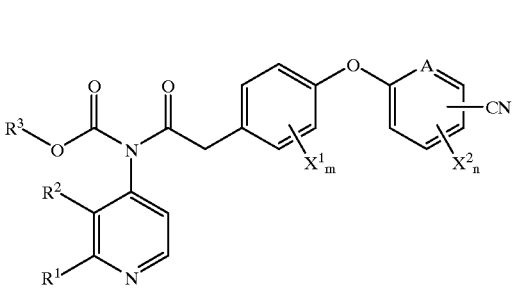

(II)

in which
$R^1$, $R^2$, $R^3$, A, $X^1$, $X^2$, m and n are as defined in claim 1, with an $R^4$ group as defined in claim 1;
wherein the step of replacing the nitrile group with a $R^4$ group comprises reacting the compound of formula (II) with one or more ingredients selected from the group consisting of alcohols, HCl, halogenoketones, hydroxylamine, ortho esters, sodium ethoxide, dibromoethane, diphenyldithiophosphinic acid, phosphorus pentasulphide and Lawessons reagent.

10. A process for preparing pesticides and fungicides comprising mixing a compound according to claim 1 with an extender and/or a surfactant.

11. A process for preparing pesticides and fungicides comprising mixing a compound of the formula (I) according to claim 2 with an extender and/or a surfactant.

12. A process according to claim 9, wherein the step of replacing the nitrile group with a $R^4$ group comprises hydrolyzing the nitrile to obtain a carboxamide.

13. A process according to claim 9, wherein the step of replacing the nitrile group with a $R^4$ group comprises reacting the compound of formula (II) with a sulphurizing agent selected from the group consisting of diphenyldithiophosphinic acid, phosphorus pentasulphide and Lawessons reagent to obtain a thioamide.

14. A process according to claim 9, wherein the step of replacing the nitrile group with a $R^4$ group comprises reacting the compound of formula (II) with a sulphurizing agent selected from the group consisting of diphenyldithiophosphinic acid, phosphorus pentasulphide and Lawessons reagent to obtain a thioamide, and subsequently reacting the thioamide with a halogenoketone to obtain a thiazole.

15. A process according to claim 9, wherein the step of replacing the nitrile group with a $R^4$ group comprises reacting the compound of formula (II) with hydroxylamine.

16. A process according to claim 9, wherein the step of replacing the nitrile group with a $R^4$ group comprises reacting the compound of formula (II) with hydroxylamine, followed by cyclizing with an ortho ester to obtain a 1,2,4-oxadiazole.

17. A process according to claim 9, wherein the step of replacing the nitrile group with a $R^4$ group comprises reacting the compound of formula (II) with HCl and an alcohol to obtain a carboxylic ester.

18. A process according to claim 9, wherein the step of replacing the nitrile group with a $R^4$ group comprises reacting the compound of formula (II) with HCl and an alcohol to obtain a carboxylic ester, and reacting the carboxylic ester with hydroxylamine and sodium ethoxide to obtain an intermediate, and subsequent cyclizing the intermediate with dibromoethane to obtain a 1,4,2-dioxazine.

* * * * *